US012755843B2

(12) United States Patent
Retzkin et al.

(10) Patent No.: US 12,755,843 B2
(45) Date of Patent: Oct. 6, 2026

(54) SYSTEM FOR COMMUNICATION WITH A PATIENT BASED ON THE DETERMINED SEDATION STATE

(71) Applicant: EYEFREE ASSISTING COMMUNICATION LTD., Tel Aviv (IL)

(72) Inventors: Or Retzkin, Tel Aviv (IL); Itai Kornberg, Lehavim (IL)

(73) Assignee: EYEFREE ASSISTING COMMUNICATION LTD., Tel Aviv (IL)

( * ) Notice: Subject to any disclaimer, the term of this patent is extended or adjusted under 35 U.S.C. 154(b) by 253 days.

(21) Appl. No.: 18/691,882

(22) PCT Filed: Jul. 21, 2022

(86) PCT No.: PCT/IL2022/050789
§ 371 (c)(1),
(2) Date: Mar. 13, 2024

(87) PCT Pub. No.: WO2023/002488
PCT Pub. Date: Jan. 26, 2023

(65) Prior Publication Data

US 2025/0095850 A1 Mar. 20, 2025

(30) Foreign Application Priority Data

Jul. 22, 2021 (IL) .......................................... 285071
May 19, 2022 (IL) .......................................... 293149

(51) Int. Cl.
*G16H 50/20* (2018.01)
*G16H 30/20* (2018.01)
*G16H 30/40* (2018.01)

(52) U.S. Cl.
CPC ............. *G16H 50/20* (2018.01); *G16H 30/20* (2018.01); *G16H 30/40* (2018.01)

(58) Field of Classification Search
CPC ......... A61B 3/112; A61B 5/163; A61B 5/369; A61B 5/4821; B60W 2040/0827;
(Continued)

(56) References Cited

U.S. PATENT DOCUMENTS 7,982,618 B2 7/2011 Omi
2007/0273611 A1 11/2007 Torch
2017/0164832 A1 6/2017 Kaib et al.

FOREIGN PATENT DOCUMENTS

JP 2005-514122 A 5/2005
JP 2007-244437 A 9/2007
(Continued)

OTHER PUBLICATIONS

Ju X. Et al. "A systematic review on voiceless patients' willingness to adopt high-technology augmentative and alternative communication in intensive care units" Nov. 2020.
(Continued)

*Primary Examiner* — Jon Eric C Morales
(74) *Attorney, Agent, or Firm* — Maschoff Brennan

(57) ABSTRACT

The present disclosure provides solutions for monitoring the sedation/cognitive state of a patient, such as an Intensive Care Unit (ICU) patient, that can be found in a plurality of sedation/cognitive states, ranging from non-responsive states to fully responsive and providing a selected interaction that is suitable for the determined state in order to optimize the interaction with the patient and, optionally, to improve his/her sedation state. The determination of the sedation state of the patient can be made by one or more sensing devices or input utilities, such as eye tracking sensor, EEG sensor or any applicable user interface.

14 Claims, 4 Drawing Sheets

(58) Field of Classification Search
CPC ........... B60W 2050/143; B60W 50/14; B60W 50/16; G08B 21/06; G06F 3/013; G06F 3/017; G16H 30/20; G16H 30/40; G16H 40/63; G16H 50/20; G16H 50/30
See application file for complete search history.

(56) References Cited

FOREIGN PATENT DOCUMENTS

| | | | |
|---|---|---|---|
| JP | 2007-531579 | A | 11/2007 |
| JP | 2008-510591 | A | 4/2008 |
| JP | 2016-512622 | A | 4/2016 |
| JP | 2018-519601 | A | 7/2018 |
| KR | 20180131045 | | 12/2018 |
| WO | 03/057296 | A1 | 7/2003 |
| WO | 2005/094667 | A2 | 10/2005 |
| WO | 2006/026528 | A2 | 3/2006 |
| WO | 2013/089236 | A1 | 6/2013 |
| WO | 2014/105678 | A1 | 7/2014 |
| WO | 2015039689 | | 3/2015 |
| WO | 2016/142933 | A1 | 9/2016 |
| WO | 2016142933 | | 9/2016 |
| WO | 2019111257 | | 6/2019 |
| WO | 2021024257 | | 2/2021 |

OTHER PUBLICATIONS

JP Office Action dated Jul. 14, 2026 as received in Application No. 2024-502519.

SYSTEM FOR COMMUNICATION WITH A PATIENT BASED ON THE DETERMINED SEDATION STATE

TECHNOLOGICAL FIELD

The present disclosure is in the field of automated system for monitoring cognitive state of a patient and communicating with him/her.

BACKGROUND ART

References considered to be relevant as background to the presently disclosed subject matter are listed below:

WO 2021/024257;

WO 2016/142933;

WO 2019/111257.

Acknowledgement of the above references herein is not to be inferred as meaning that these are in any way relevant to the patentability of the presently disclosed subject matter.

GENERAL DESCRIPTION

A first part of the present disclosure provides a system and a method for interacting with a patient that can be found in a plurality of sedation/cognitive states, ranging from non-responsive states to fully responsive. The terms sedation state and cognitive state are interchangeable, and they both refer to the awareness state of the patient and his/her ability to communicate with the surrounding. The system and the method provide a solution that is adapting the type of communication provided to the patient according to his/her sedation state. This is done to ensure that the communication is effective and there is a reasonable chance that the patient receives and able to process the communication, and in times to respond it. Such adapted communication has much more chance to improve the sedation state of the patient.

Therefore, an aspect of the present disclosure provides a system for interacting with a patient. The system comprising a communication module configured to operate in at least three communication modes that comprises: (i) unidirectional mode, in which the communication module outputs communication to the patient that does not require his/her response. This communication is relevant when the patient is in a sedation state with no capability to respond; (ii) responsive mode, in which the communication module outputs communication to the patient the requires his/her response. This may include questions to or requests from the patient. This communication is relevant when the patient has the capability to respond to communication but lacks the capability to initiate the communication; and (iii) open communication mode, in which the communication module allows the patient to proactively initiate communication with the system. This communication can be in various forms, for example the patient may request from the system to play music, to communicate with clinicians, caregivers, family members, to watch video or the like.

The system further comprising a processing circuitry that comprises an input module configured to receive input data indicative of the patient sedation state. The processing circuitry is configured to (1) determine the sedation state of the patient based on the input data; and (2) triggering the communication module to operate in a selected communication mode in response to the determined sedation state and output a selected communication scheme based thereon.

The following are various embodiments of the system. It is appreciated that, unless specifically stated otherwise, certain features of the presently disclosed subject matter, which are, for clarity, described in the context of separate embodiments, may also be provided in any combination in a single embodiment.

In some embodiments of the system, the communication module is configured to perform and/or allow the patient (i) audible communication, namely output a communication protocol to the patient audibly and also being capable to receive audio commands, (ii) video-based communication, namely to output a video to the patient on a screen, (iii) eye-based communication, namely a camera that records the eyes of the patient and the system classify the eye movements of the patient to distinguished gesture that allows communication with the system, (iv) touch-screen based communication, namely the patient can communicate through a touch screen, (v) tactile communication, (vi) EEG-based communication, namely communication that is based on detection of EEG signals of the patient, e.g. signals received by an EEG unit coupled to the head of the patient, (vii) EOG-based communication, namely communication that is based on detection of EOG signals of the patient, (viii) automatic lip-reading communication, i.e. a camera that records images of the lips of the patient and the processing circuitry is configured to determine from these lips images the words pronounced by the patient and record it as communication of the patient, (ix) head gestures-based communication, i.e. a camera that records images of the head of the patient and the processing circuitry is configured to determine from these head images head gestures that are classified into specific communication performed by the patient, (x) or any combination thereof. These communications are allowed as part of the outputted communication to the patient in response to the determined sedation state.

In some embodiments of the system, the determination of the sedation state of the patient based on the input data comprises classifying the sedation state of the patient into at least three sedation levels, each level triggers one or more level-specific communication modes.

In some embodiments of the system, said classifying comprises scoring the sedation state of the patient, the score defines the sedation level. There are at least three ranges of scores, each range defines a different level. It is to be noted that two level can have overlapping scores.

In some embodiments of the system, the scoring is a Richmond Agitation-Sedation Scale (RASS) score. For example, score of −2 or less and +3 and above triggers the unidirectional mode, a score between and including −1 to +2 triggers the responsive mode and a score between and including 0 to +1, which overlaps with the second range score, triggers an open communication mode. The open communication mode can be operated alone or in combination with the responsive mode in a certain communication protocol profile.

In some embodiments of the system, the processing circuitry is configured to apply at least one or any combination of the following:

- trigger the unidirectional mode upon determining a non-responsive sedation state of the patient;
- trigger the responsive mode and/or the unidirectional mode upon determining a low-level responsive sedation state of the patient;
- trigger the open communication mode and/or the responsive mode and/or the unidirectional mode upon determining a high-level responsive sedation state of the patient.

In some embodiments of the system, the selection of the communication mode is intended to improve the sedation state of the patient.

In some embodiments of the system, the sedation state of the patient is indicative of or the actual delirium state of the patient.

In some embodiments of the system, said input data comprises recorded communication of the patient with the communication module.

In some embodiments of the system, said input data comprises eye image data indicative of recorded images of an eye of the patient.

In some embodiments, the system comprising a camera unit configured for recording images of an eye of the patient and generating eye image data based thereon, wherein said input data comprises said image data.

In some embodiments of the system, said input data comprises EEG data indicative of recorded EEG signals of the patient.

In some embodiments, the system comprising an EEG unit configured for recording EEG signals of the patient and generate EEG data based thereon, said input data comprises said EEG data.

Yet another aspect of the present disclosure provides a method for interacting with a patient. The method comprising

- input data indicative of the patient sedation state;
- determining based on the input data the sedation state of the patient; and
- in response to the determined sedation state of the patient, outputting a selected communication in a communication mode selected from at least one of three communication modes that comprises: unidirectional mode, responsive mode, and open communication mode. These three modes are defined above with respect to the system aspect and these definitions also apply here.

In some embodiments of the method, said selected communication is any one of audible communication, video-based communication, eye-based communication, touch-screen-based communication, tactile communication, EEG-based communication, EOG-based communication, automatic lip-reading communication, head gestures-based communication, or any combination thereof.

In some embodiments of the method, the determination of the sedation state of the patient based on the input data comprises classifying the sedation state of the patient into at least three sedation levels, each level triggers one or more level-specific communication modes.

In some embodiments of the method, said classifying comprises scoring the sedation state of the patient, the score defines the sedation level. There are at least three ranges of scores, each range defines a different level. It is to be noted that two level can have overlapping scores.

In some embodiments of the method, the scoring is a Richmond Agitation-Sedation Scale (RASS) score. For example, score of −2 or less and +3 and above triggers the unidirectional mode, a score between and including −1 to +2 triggers the responsive mode and a score between and including 0 to +1, which overlaps with the second range score, triggers an open communication mode. The open communication mode can be operated alone or in combination with the responsive mode in a certain communication protocol profile.

In some embodiments of the method, said outputting comprising at least one or any combination of the following:

- selecting the unidirectional mode upon determining a non-responsive sedation state of the patient;
- selecting the responsive mode and/or the unidirectional mode upon determining a low-level responsive sedation state of the patient;
- selecting the open communication mode and/or the responsive mode and/or the unidirectional mode upon determining a high-level responsive sedation state of the patient.

In some embodiments of the method, the selection of the communication mode is intended to improve the sedation state of the patient.

In some embodiments of the method, the sedation state of the patient is indicative of or the actual delirium state of the patient.

In some embodiments of the method, said input data comprises recorded communication of the patient with the communication module.

In some embodiments of the method, said input data comprises eye image data indicative of recorded images of an eye of the patient.

In some embodiments of the method, said input data comprises EEG data indicative of recorded EEG signals of the patient.

Another part of the present disclosure provides a system for monitoring the sedation/cognitive state of a patient by continuously monitoring the patient's eye activity and generating eye image date based thereon. The monitor is further configured to provide a selected output to the patient, such as a questionnaire, an audible output and/or a visual output, in order to increase his/her awareness and reduce risks or state of delirium.

Optionally, the system is configured to receive EEG data indicative of recorded EEG signals of the patient that are time-correlated with the recorded eye activity of the patient, and the sedation state of the patient is determined based on either the EEG data, the eye image data or combination thereof. Different sedation states of the patient can be determined by applying different weight factors profiles of the two sets of data.

Upon determination of the sedation state of the patient, the processing circuitry, i.e. the processor/controller of the system, is configured to operate a communication module so as to trigger a selected output of engaging communication to the patient. The output may be interactive, namely one that requires a response from the patient, or passive that only needs to be received by one of the senses of the patient without any required response therefrom. The outputted communication is intended to stimulate the cognitive activity of the patient and thereby improving his/her cognitive state.

Thus, as aspect of the present disclosure provides a system for monitoring sedation level of a patient. The system includes (1) a camera unit configured for recording images of an eye of the patient and generating eye image data based thereon; (2) a communication module operable to output a desired communication protocol; and (3) a processing circuitry. The processing circuitry comprises an input module configured to receive EEG data indicative of EEG signal of the patient and is in data communication with the camera. The processing circuitry is configured to: (i) receive and process said eye image data and EEG data; (ii) determine based on at least one of the eye image data and EEG data the sedation or cognitive state of the user; and (iii) triggering the communication module to output a selected communication protocol in response to the determined sedation state. The communication protocol can be a questionnaire, playing of music, outputting recorded audio of family or friend, etc.

Yet another aspect of the present disclosure provides a system for monitoring sedation level of a patient. The system comprising (1) a camera unit configured for recording images of an eye of the patient and generating eye image data based thereon; (2) a communication module operable to output a desired communication protocol; and (3) a processing circuitry. The processing circuitry is in data communication with the camera and is operable to (i) receive and process said eye image data; (ii) determine based on the eye image data the sedation or cognitive state of the user; and (iii) triggering the communication module to output a selected communication protocol in response to the determined sedation state. The communication protocol can be a questionnaire, playing of music, outputting audio of family or friends, etc.

The following are optional embodiments for any of the above-described aspects. It is appreciated that, unless specifically stated otherwise, certain features of the presently disclosed subject matter, which are, for clarity, described in the context of separate embodiments, may also be provided in any combination in a single embodiment.

In some embodiments, the system further comprising an EEG unit configured for recording EEG signals of the patient and generate said EEG data based thereon.

It is to be noted that any combination of the described embodiments with respect to any aspect of this present disclosure is applicable. In other words, any aspect of the present disclosure can be defined by any combination of the described embodiments.

In some embodiments of the system, the processing circuitry is configured to calculate a sedation score of the patient, such as Richmond Agitation-Sedation Scale (RASS) score, and to classify the score into two or more score ranges, each range triggers a different communication protocol.

In some embodiments of the system, in at least one range of scores, the determination of the sedation state and/or the communication protocol is triggered only based on the EEG data. Thus, in a score that indicates that the patient is sedated and there is no eye activity that can be monitored by the camera unit, the sedation state of the patient is determined only based on the EEG data.

In some embodiments of the system, in at least one range of scores the determination of the sedation state and/or the communication protocol is triggered based on a combination of the eye image data and the EEG data. Namely, in a score that indicates that the patient is alerted at some level and there is eye activity that can be monitored by the camera unit, the determination of the sedation state of the patient is determined based on a certain level of combination of the two data sets. Depending on the recorded activity of the eye and the brain of the patient, the influence of each data for determining the sedation is determined by the processing unit. Typically, when the patient is responsive to some extent and there is eye activity, the eye image data is more significant for the determination of the sedation state.

In some embodiments of the system, the processing circuitry is configured to determine the sedation state of the user by continuously classifying the recorded eye activity of the patient into defined gestures. The temporal profile of the eye gestures defines the sedation state of the patient.

In some embodiments of the system, the processing circuitry is configured for applying different and varying weight factors to the EEG data and the eye image data based on the amount of information or the assumed sedation state of the patient. Namely, during a certain time period, the processing circuitry is configured to apply weight factors on the data sets obtained by the EEG sensor, or the image sensor based on the most recent determined sedation state and/or based on the amount of varying information received by the EEG sensor or image sensor in the certain time period.

In some embodiments of the system, the processing circuitry is configured to apply weight factors on the EEG data and the eye image data based on the recent determined sedation state and update the weight factors when a change of the sedation state is identified. Therefore, when the patient is in a sedation state in which the eye activity is negligible, the weight factors on the EEG data are much more significant and in a sedation state in which there is a significant eye activity by the user, the weight factor of the eye image data increases significantly.

In some embodiments of the system, the processing circuitry is configured to apply a temporal analysis on the eye image data and the EEG data to determine a correlation between eye movements, brain activity and sedation level. This can be performed by applying a machine learning algorithm and training the system by inputting the sedation score level at different scenarios of eye movements and brain activity.

In some embodiments of the system, the processing circuitry is configured to analyze selected time-windows of the eye image data and/or the EEG data following an output of communication protocol to identify patient's response to said communication protocol and to determine an updated sedation state of the patient based on said response.

In some embodiments of the system, the processing circuitry is further configured to transmit a signal carrying sedation state data indicative of the sedation state of the patient to a remote unit. This can be performed through a transmitting unit of the processing circuitry.

In some embodiments of the system, the processing circuitry is further configured to identify specific eye gestures in said eye image data. The eye gestures either trigger a communication protocol or affecting a selected communication protocol. Namely, the identified eye gesture can be used for execution commands in the system and/or to be used to analyze the sedation state of the patient to adapt the relevant communication protocol.

Throughout the specification, an eye gesture should be interpreted as an identified gesture of the eye out of many possible eye gestures. For example, an eye gesture can be a movement of the iris to a certain direction (up, down, right, or left), blinking, steady gaze direction, round movement of the iris, sequence of specific eye gestures, etc.

In some embodiments of the system, the processing circuitry is configured to classify the eye gestures into responses of the patient to a questionnaire. For example, the questionnaire can be Confusion Assessment Method for the Intensive Care Unit (CAM-ICU that is outputted to the patient audibly and the patient respond to each question in the questionnaire with a specific eye gesture that indicates a specific response of the patient to the question.

In some embodiments of the system, the processing circuitry is configured to classify the eye gestures as commands for playing audible output. The audible output is selected from certain music and voice recording of relatives, such as greetings of friends and family.

In some embodiments of the system, the processing circuitry is configured to analyze said eye image and EEG data and identify signatures, namely certain temporal pattern of eye activity, brain activity or a combination thereof, which are indicative of clinical state of the patient.

In some embodiments of the system, the processing circuitry is configured to correlate temporal profiles of said eye image data and/or EEG data with predetermined temporal profiles corresponding to a plurality of signatures, which are indicative of a plurality of clinical states, and to identify a correlation that satisfies a certain condition, such as best match or a certain threshold of matching. The predetermined temporal profiles are stored in a predetermined database and the processing circuitry is in data communication with said predetermined database. In some embodiments, the system further includes said predetermined database.

In some embodiments of the system, the processing circuitry is configured to update the database or to store in a memory thereof so as to generate a personalized signature of the patient upon identifying it. The identification of the personalized signature may be from a clinical indication that is inputted to the system or by manual indication inputted by a user that identifies a certain temporal pattern with the clinical state of the patient.

In some embodiments of the system, the clinical condition is selected from at least one of: pain, thirst, hunger, delirium.

Yet another aspect of the present disclosure provides a method for monitoring sedation state of a patient. The method comprising:

- receiving and processing (i) eye image data indicative of recorded images of an eye of the patient and (ii) EEG data indicative of EEG signal of the patient;
- determining based on at least one of the eye image data and EEG data the sedation state of the user; and
- outputting a selected communication protocol in response to the determined sedation state.

In some embodiments, the method further comprising calculating a sedation score of the patient and classifying the score into two or more score ranges, each range triggers a different output of communication protocol.

In some embodiment of the method, in at least one range of scores the determination of the sedation state and/or the communication protocol is triggered only based on the EEG data.

In some embodiments of the method, in at least one range of scores the determination of the sedation state and/or the communication protocol is triggered based on a combination of the eye image data and the EEG data.

In some embodiments, the method comprising determining the sedation state of the user by continuously classifying the recorded eye activity of the patient into defined gestures. The temporal profile of the eye gestures defines the sedation state of the patient.

In some embodiments, the method further comprising applying temporal analysis on the eye image data and the EEG data and determining a correlation between eye movements, brain activity and sedation state.

In some embodiments, the method comprising applying different and varying weight factors to the EEG data and the eye image data based on the amount of information or the assumed sedation state of the patient. Namely, during a certain time period, the method comprises applying weight factors on the data sets obtained by the EEG sensor, or the image sensor based on the most recent determined sedation state and/or based on the amount of varying information received by the EEG sensor or image sensor in the certain time period.

In some embodiments, the method comprising applying weight factors on the EEG data and the eye image data based on the recent determined sedation state and update the weight factors when a change of the sedation state is identified. Therefore, when the patient is in a sedation state in which the eye activity is negligible, the weight factors on the EEG data are much more significant and in a sedation state in which there is a significant eye activity by the user, the weight factor of the eye image data increases significantly.

In some embodiments, the method comprising analyzing selected time-windows of the eye image data and/or the EEG data following an output of communication protocol to identify patient's response to said communication protocol and to determine an updated sedation state of the patient based on said response.

In some embodiments, the method comprising transmitting a signal carrying sedation state data indicative of the sedation state of the patient to a remote unit.

In some embodiments, the method further comprising identifying eye gestures in said eye image data and either triggering a communication protocol or affecting the selected communication protocol based on said eye gestures. Namely, the identified eye gesture can be used for execution commands in the system and/or to be used to analyze the sedation state of the patient to adapt the relevant communication protocol.

In some embodiments of the method, said eye gestures are used for patient's response to a questionnaire.

In some embodiments of the method, said eye gestures are used for playing audible output, said audible output is selected from certain music and voice recording of relatives.

In some embodiments, the method comprising analyzing said eye image and EEG data and identify signatures indicative of clinical state of the patient.

In some embodiments, the method comprising correlating temporal profiles of said eye image data and/or EEG data with predetermined temporal profiles corresponding to a plurality of signatures that are stored in a database and identifying a correlation that satisfies a certain condition.

In some embodiments of the method, the clinical condition is selected from at least one of: pain, thirst, hunger, delirium.

In some embodiments, the method comprising generating a personalized signature of the patient and updating said database or storing in a memory said personalized signature.

EMBODIMENTS

The following are optional embodiments and combinations thereof in accordance with aspects of the present disclosure:

1. A system for interacting with a patient, comprising:
   - a communication module configured to operate in at least three communication modes that comprises: unidirectional mode, responsive mode and open communication mode;
   - a processing circuitry that comprises an input module configured to receive input data indicative of the patient sedation state, the processing circuitry is configured to
     - i. determine the sedation state of the patient based on the input data;
     - ii. triggering the communication module to operate in a selected communication mode in response to the determined sedation state.

2. The system of embodiment 1, wherein the communication module is configured to perform and/or allow the patient audible communication, video-based communication, eye-based communication, touch-screen based communication, tactile communication, EEG-based communication, EOG-based communication, automatic lip-reading communication, head gestures-based communication or any combination thereof.

3. The system of embodiment 1 or 2, wherein the determination of the sedation state of the patient based on the input data comprises classifying the sedation state of the patient into at least three sedation levels, each level triggers one or more level-specific communication modes.

4. The system of embodiment 3, wherein said classifying comprises scoring the sedation state of the patient, the score defines the sedation level.

5. The system of embodiment 4, wherein the scoring is a Richmond Agitation-Sedation Scale (RASS) score.

6. The system of any one of embodiments 1-5, wherein the processing circuitry is configured to:

trigger the unidirectional mode upon determining a non-responsive sedation state of the patient;

trigger the responsive mode and/or the unidirectional mode upon determining a low-level responsive sedation state of the patient;

trigger the open communication mode and/or the responsive mode and/or the unidirectional mode upon determining a high-level responsive sedation state of the patient.

7. The system of any one of embodiments 1-6, wherein the selection of the communication mode is intended to improve the sedation state of the patient.

8. The system of any one of embodiments 1-7, wherein the sedation state of the patient is the delirium state of the patient.

9. The system of any one of embodiments 1-8, wherein said input data comprises recorded communication of the patient with the communication module.

10. The system of any one of embodiments 1-9, wherein said input data comprises eye image data indicative of recorded images of an eye of the patient.

11. The system of any one of embodiments 1-10, comprising a camera unit configured for recording images of an eye of the patient and generating eye image data based thereon, wherein said input data comprises said image data.

12. The system of any one of embodiments 1-11, wherein said input data comprises EEG data indicative of recorded EEG signals of the patient.

13. The system of any one of embodiments 1-12, comprising an EEG unit configured for recording EEG signals of the patient and generate EEG data based thereon, said input data comprises said EEG data.

14. A method for interacting with a patient, comprising:

receiving and processing input data indicative of the patient sedation state;

determining based on the input data the sedation state of the patient; and in response to the determined sedation state of the patient, outputting a selected communication in a communication mode selected from at least one of three communication modes that comprises: unidirectional mode, responsive mode and open communication mode.

15. The method of embodiment 14, wherein said selected communication is any one of audible communication, video-based communication, eye-based communication, touch-screen-based communication, tactile communication, EEG-based communication, EOG-based communication, automatic lip-reading communication, head gestures-based communication, or any combination thereof.

16. The method of embodiment 14 or 15, wherein the determination of the sedation state of the patient based on the input data comprises classifying the sedation state of the patient into at least three sedation levels, each level triggers one or more level-specific communication modes.

17. The method of embodiment 16, wherein said classifying comprises scoring the sedation state of the patient, the score defines the sedation level.

18. The method of embodiment 17, wherein the scoring is a Richmond Agitation-Sedation Scale (RASS) score.

19. The method of any one of embodiments 15-18, wherein said outputting comprising:

selecting the unidirectional mode upon determining a non-responsive sedation state of the patient;

selecting the responsive mode and/or the unidirectional mode upon determining a low-level responsive sedation state of the patient;

selecting the open communication mode and/or the responsive mode and/or the unidirectional mode upon determining a high-level responsive sedation state of the patient.

20. The method of any one of embodiments 15-19, wherein the selection of the communication mode is intended to improve the sedation state of the patient.

21. The method of any one of embodiments 15-20, wherein the sedation state of the patient is the delirium state of the patient.

22. The method of any one of embodiments 15-21, wherein said input data comprises recorded communication of the patient with the communication module.

23. The method of any one of embodiments 15-22, wherein said input data comprises eye image data indicative of recorded images of an eye of the patient.

24. The method of any one of embodiments 15-23, wherein said input data comprises EEG data indicative of recorded EEG signals of the patient.

25. A system for monitoring sedation state of a patient, the system comprising:

a camera unit configured for recording images of an eye of the patient and generating eye image data based thereon;

a communication module operable to output a desired communication protocol;

a processing circuitry that comprises an input module configured to receive EEG data indicative of EEG signal of the patient, the processing circuitry is in data communication with the camera and being operable to i. receive and process said eye image data and EEG data;

ii. determine based on at least one of the eye image data and EEG data the sedation state of the patient;

iii. triggering the communication module to output a selected communication protocol in response to the determined sedation state.

26. The system of embodiment 25, comprising an EEG unit configured for recording EEG signals of the patient and generate said EEG data based thereon.

27. The system of embodiment 25 or 26, wherein the processing circuitry is configured to calculate a sedation score of the patient and to classify the score into two or more score ranges, each range triggers a different communication protocol.

28. The system of embodiment 27, wherein in at least one range of scores the determination of the sedation state and/or the communication protocol is triggered only based on the EEG data.

29. The system of embodiment 27 or 28, wherein in at least one range of scores the determination of the sedation state and/or the communication protocol is triggered based on a combination of the eye image data and the EEG data.

30. The system of any one of embodiments 25-29, wherein the processing circuitry is configured to apply a temporal analysis on the eye image data and the EEG data to determine a correlation between eye movements, brain activity and sedation state.

31. The system of any one of embodiments 25-30, wherein the processing circuitry is configured to analyze selected time-windows of the eye image data and/or the EEG data following an output of communication protocol to identify patient's response to said communication protocol and to determine an updated sedation state of the patient based on said response.

32. The system of any one of embodiments 25-31, wherein the processing circuitry is further configured to transmit a signal carrying sedation state data indicative of the sedation state of the patient to a remote unit.

33. The system of any one of embodiments 25-32, wherein the processing circuitry is further configured to identify eye gestures in said eye image data, said eye gestures either trigger a communication protocol or affecting a selected communication protocol.

34. The system of embodiment 33, wherein said eye gestures are used for patient's response to a questionnaire.

35. The system of embodiment 33 or 34, wherein said eye gestures are used for playing audible output, said audible output is selected from certain music and voice recording of relatives.

36. The system of any one of embodiments 25-35, wherein the processing circuitry is configured to analyze said eye image and EEG data and identify signatures indicative of clinical state of the patient.

37. The system of embodiment 36, wherein the processing circuitry is configured to correlate temporal profiles of said eye image data and/or EEG data with predetermined temporal profiles corresponding to a plurality of signatures that are stored in a database and to identify a correlation that satisfies a certain condition.

38. The system of embodiment 36 or 37, wherein the clinical condition is selected from at least one of: pain, thirst, hunger, delirium.

39. The system of any one of embodiments 36-38, wherein the processing circuitry is configured to generate a personalized signature of the patient upon identifying it and update the database or to store in a memory thereof said personalized signature of the patient.

40. The system of any one of embodiments 25-39, wherein the processing circuitry is configured for applying different and varying weight factors to the EEG data and the eye image data based on the amount of information or the assumed sedation state of the patient.

41. The system of any one of embodiments 25-40, wherein the processing circuitry is configured to apply weight factors on the EEG data and the eye image data based on the recent determined sedation state and update the weight factors upon a change of the sedation state is identified.

42. The system of any one of embodiments 25-41, wherein the processing circuitry is configured to determine the sedation state of the user by continuously classifying the recorded eye activity of the patient into defined gestures, the temporal profile of the eye gestures defines the sedation state of the patient.

43. A system for monitoring sedation state of a patient, the system comprising:

a camera unit configured for recording images of an eye of the patient and generating eye image data based thereon;

an EEG unit configured for recording EEG signals of the patient and generate EEG data based thereon;

a communication module; and a processing circuitry in data communication with the camera and EEG unit and being operable to i. receive and process said eye image data and EEG data;

ii. determine based on at least one of the eye image data and EEG data the sedation state of the user;

iii. triggering the communication module to output a selected communication protocol in response to the determined sedation state.

44. A system for monitoring sedation state of a patient, the system comprising:

a camera unit configured for recording images of an eye of the patient and generating eye image data based thereon;

a communication module operable to output a desired communication protocol;

a processing circuitry in data communication with the camera and being operable to i. receive and process said eye image data;

ii determine based on the eye image data the sedation state of the user;

iii. triggering the communication module to output a selected communication protocol in response to the determined sedation state.

45. A method for monitoring sedation state of a patient, comprising:

receiving and processing (i) eye image data indicative of recorded images of an eye of the patient and (ii) EEG data indicative of EEG signal of the patient;

determining based on at least one of the eye image data and EEG data the sedation state of the user; and outputting a selected communication protocol in response to the determined sedation state.

46. The method of embodiment 45, comprising calculating a sedation score of the patient and classifying the score into two or more score ranges, each range triggers a different output of communication protocol.

47. The method of embodiment 46, wherein in at least one range of scores the determination of the sedation state and/or the communication protocol is triggered only based on the EEG data.

48. The method of embodiment 47, wherein in at least one range of scores the determination of the sedation state and/or the communication protocol is triggered based on a combination of the eye image data and the EEG data.

49. The method of any one of embodiments 45-48, comprising applying temporal analysis on the eye image data and the EEG data and determining a correlation between eye movements, brain activity and sedation state.

50. The method of any one of embodiments 45-49, comprising analyzing selected time-windows of the eye image data and/or the EEG data following an output of communication protocol to identify patient's response to said communication protocol and to determine an updated sedation state of the patient based on said response.

51. The method of any one of embodiments 45-50, comprising transmitting a signal carrying sedation state data indicative of the sedation state of the patient to a remote unit.

52. The method of any one of embodiments 45-51, further comprising identifying eye gestures in said eye image data and either triggering a communication protocol or affecting the selected communication protocol based on said eye gestures.

53. The method of embodiment 52, wherein said eye gestures are used for patient's response to a questionnaire.

54. The method of embodiment 52 or 53, wherein said eye gestures are used for playing audible output, said audible output is selected from certain music and voice recording of relatives.

55. The method of any one of embodiments 45-54, comprising analyzing said eye image and EEG data and identify signatures indicative of clinical state of the patient.

56. The method of embodiment 55, comprising correlating temporal profiles of said eye image data and/or EEG data with predetermined temporal profiles corresponding to a plurality of signatures that are stored in a database and identifying a correlation that satisfies a certain condition.

57. The method of embodiment 55 or 56, wherein the clinical condition is selected from at least one of: pain, thirst, hunger, delirium.

58. The method of any one of embodiments 55-57, comprising generating a personalized signature of the patient and updating said database or storing in a memory said personalized signature.

59. The method of any one of embodiments 45-58, wherein said determining comprises applying different and varying weight factors to the EEG data and the eye image data based on the amount of information or the assumed sedation state of the patient.

60. The method of any one of embodiments 45-59, wherein said determining comprises applying weight factors on the EEG data and the eye image data based on the recent determined sedation state and update the weight factors upon a change of the sedation state is identified.

61. The method of any one of embodiments 45-60, wherein said determining comprises determining the sedation state of the user by continuously classifying the recorded eye activity of the patient into defined gestures, the temporal profile of the eye gestures defines the sedation state of the patient.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

The following figures are provided to exemplify embodiments and realization of the invention of the present disclosure.

Reference is being made to FIGS. 1A-1D, which are non-limiting example of different embodiments of the system for monitoring the sedation level of a patient and engaging the patient with a selected engagement protocol based on the monitored sedation level. It is to be noted that the term "sedation level" is interchangeable with the term "cognitive level", "sedation state", or "cognitive state" and they all refer to a certain sedation/cognitive scale, such as, but not limited to, Richmond Agitation-Sedation Scale (RASS) score. The RASS score indicates what is the patient condition on the scale between "unarousable", in which the patient does not respond to voice or physical stimulation and "combative", in which the patient is fully aware and is overtly combative or violent.

Figure 1A:
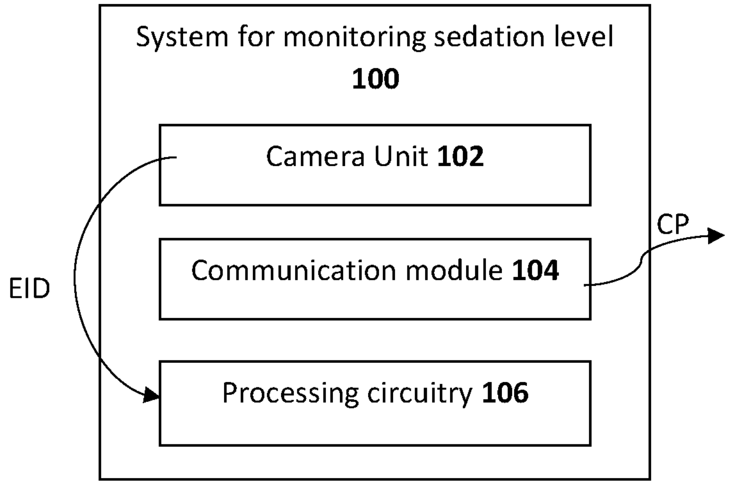
FIGS. 1A-1D are block diagrams of different non-limiting embodiments of the system according to an aspect of the present disclosure.

FIG. 1A exemplifies a system 100 that includes a camera unit 102 that is configured to continuously image and record the eye of the patient and generate eye image data EID indicative of the recorded eye images of the patient. By monitoring the activity of the eye of the patient, the sedation state of the patient can be deduced. This is performed by continuously classifying the recorded eye activity of the patient into defined gestures. The temporal profile of the eye gestures defines the sedation state of the patient.

The system further includes a communication module 104 that is configured to output a selected communication protocol CP to the patient in response to the determined sedation state of the patient by the monitoring system 100. The communication module 104 comprises a plurality of predetermined communication protocols CPs and a specific protocol is selected in response to the determined sedation state based on best match criteria. Namely, for each specific sedation state, there is a specific communication protocol. The communication protocol can be tailor-made to the patient, namely that a personalized content is outputted in the communication protocol CP to the patient. The communication protocol can include various types of communications, some of them are interactive communications, namely communications that require the patient response, and some of the communication protocols CPs are constituted by mere output of the communication module that does not require the patient's response.

A processing circuitry 106 is configured to receive the eye image data EID from the camera unit 102 and process it to determine the temporal profile of the eye gestures made by the patient. Based on identification of signatures in the temporal profile of the eye gestures, the sedation level of the patient is determined. Once the sedation level is determined, the processing circuitry is configured to operate the communication module 104 to output a selected communication protocol CP to the patient, based on the determined sedation level of the patient. When the communication protocol CP is outputted, the camera unit 102 proceeds to record the activity of the eye of the patient and generate eye image data. This new eye image data EID is processed by the processing circuitry 106 to determine, by analyzing the temporal profile of the eye gestures made by the patient in a time-window following the output of the communication protocol CP, an updated sedation state of the patient and to identify whether the communication protocol CP is affecting the sedation state of the patient. By analyzing the response of the patient to communication protocols over time, the processing circuitry can learn how to better match the best communication protocol to the patient to achieve the best progress in the sedation scale of the patient.

Figure 1B:
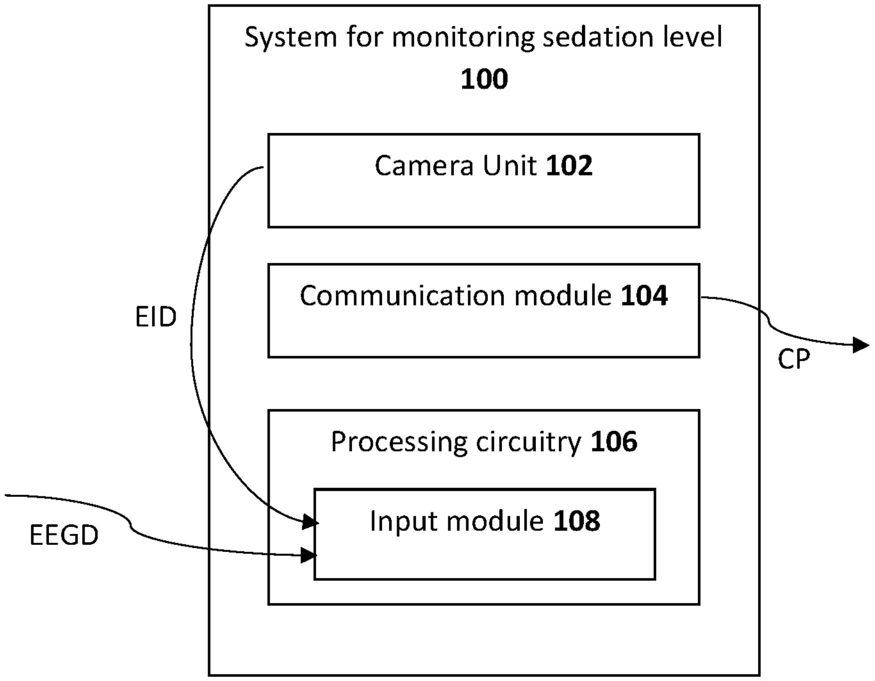

FIG. 1B is another example of the system, differs from that of FIG. 1A by including an input module 108 in the processing circuitry 106. The input module 108 is configured to receive the eye image data EID that is generated by the camera unit 102 and further receive EEG data EEGD indicative of EEG signals of the patient that his/her eye activity is being monitored by the system 100. In this example, the EEG data EEGD is generated by an EEG unit that is external to the system 100 and not part of it. The processing circuitry 106 is configured to determine the sedation state of the patient based on the EEG data EEGD and the eye image data EID. Namely, the processing circuitry is configured to assign different weight factors to each data set (EEG data EEGD and the eye image data EID) based on the amount of information or the assumed sedation state of the patient. When the patient is at a low sedation score and the eyes of the patient are not responsive, the processing circuitry assigns great weight factors to the EEG data, and when the patient sedations score rises, the weight factors of the eye image data EID rise correlatively. Thus, the EEG data EEGD is of great importance when the sedation state cannot be determined by analyzing the eye activity of the patient, namely below a certain sedation score. It is to be noted that the processing circuitry is configured to update continuously the weight factors for each patient so as to generate personalized weight factors. In other words, while there are default weight factors at the beginning of the monitoring for each new patient, the processing circuitry is configured to update the weight factors to be tailor-made for each patient. The processing circuitry may apply a machine learning algorithm to calculate and update the new weight factors.

Figure 1C:
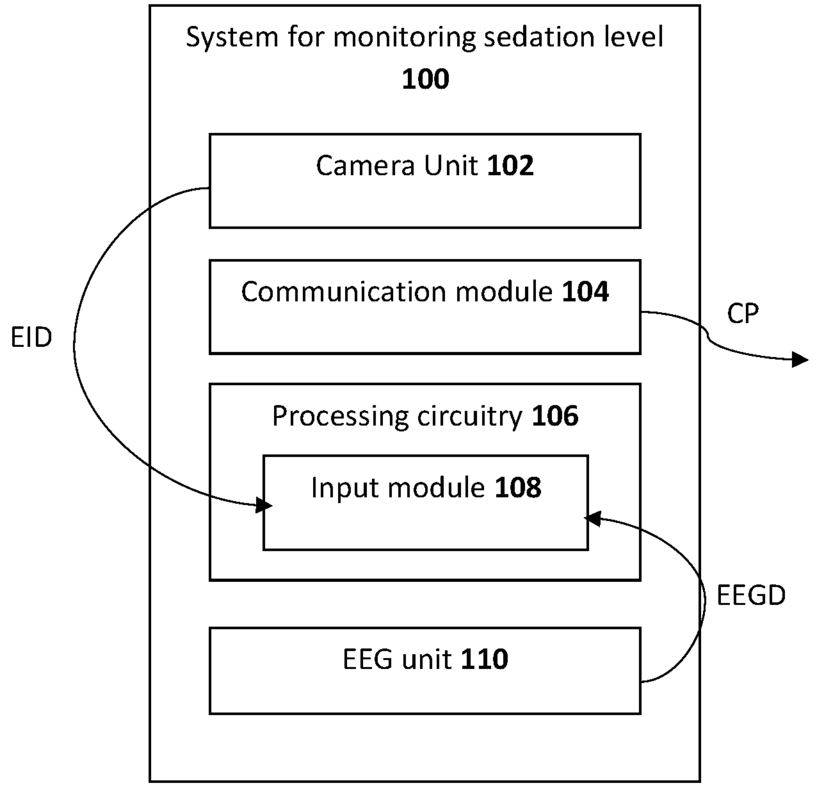

Reference is now being made to FIG. 1C, which is another example of the monitoring system of the present disclosure. This example differs from that of FIG. 1B by including the EEG unit 110 that generates the EEG data EEGD indicative of EEG signals of the monitored patient. The EEG unit 110 is configured to continuously record the brain waves activity of the patient and generate the EEG data EEGD based thereon, which is transmitted to the input module 108 of the processing circuitry 106 to assist in the determination of the sedation level of the patient.

Figure 1D:
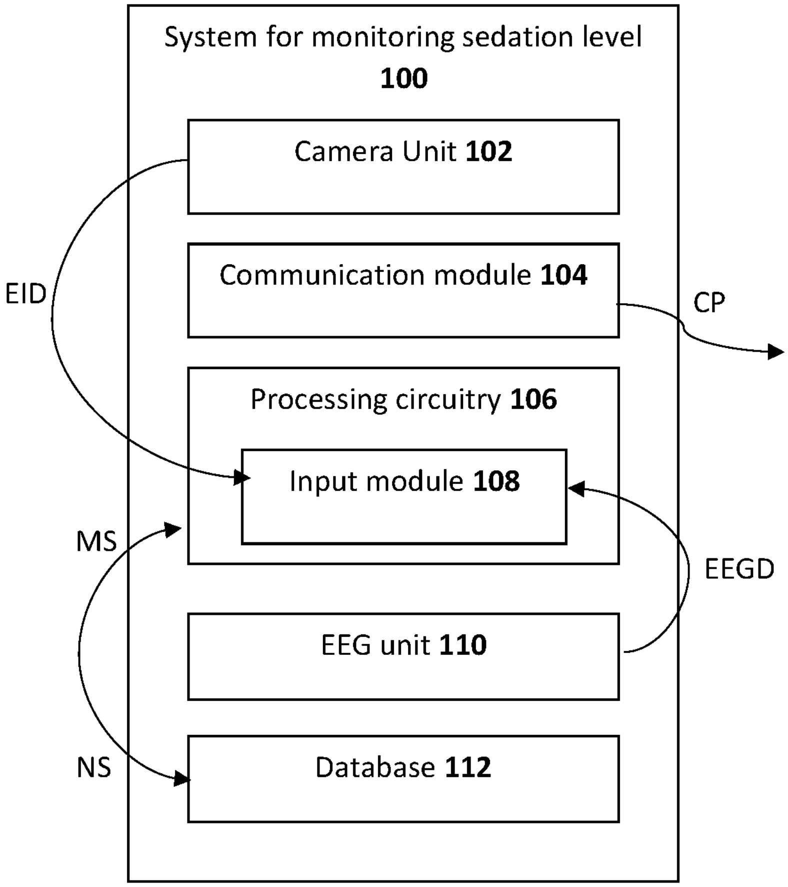

FIG. 1D is another example of the monitoring system of the present disclosure. The system of this example differs from that of FIG. 1C by including a database 112 that stores a plurality of predetermined signatures of patterns of EEG and eye image data that are each correlated with a specific medical condition of a patient. The predetermined signatures were collected from various patients or were synthetically generated, and each of them is assigned with a medical condition such that the processing circuitry 106 can apply a correlation or matching algorithm on the collected eye image data and EEG data to find a matching signature MS in the database and based on that determine the medical condition of the patient. The processing circuitry 106 can record to the database 112 a new signature NS that is collected from the monitored patient. It is to be noted that the database 112 may be physically connected to the processing circuitry 106 or can be located on a remote cloud server and communicate with the processing circuitry 106 through standard network protocols.

Figure 2A:
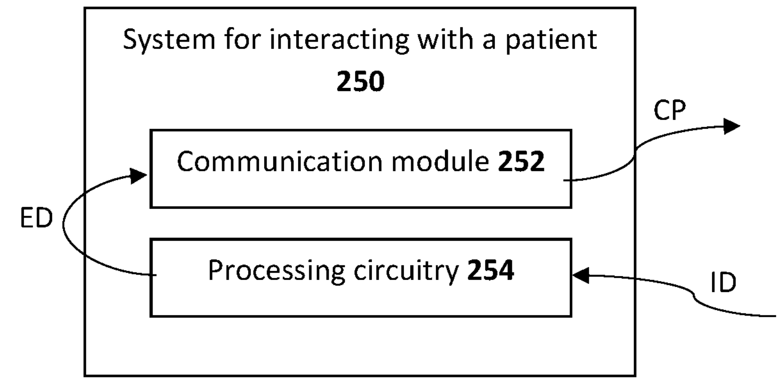
FIGS. 2A-2B are block diagrams of different non-limiting embodiments of the system according to another aspect of the present disclosure.
Figure 2B:
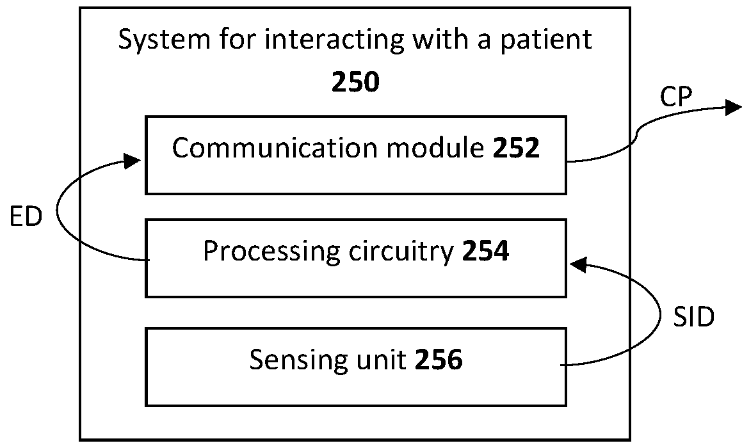

Reference is now being made to FIGS. 2A-2B, which are block diagrams of different embodiments of non-limiting examples of a system for interacting with a patient according to an aspect of the present disclosure. FIG. 2A shows a system 250 that comprises a communication module 252 and a processing circuitry 254. The communication module is configured to output a selected communication protocol CP in one or more types of communication modes, selected from (i) unidirectional mode, which is a communication that is outputted to the patient without expectation for his/her response, (ii) responsive mode, which is a communication that is outputted to the patient and requires his/her response so the communication module is designed to receive the communication response from the patient (e.g. through a touchscreen, a reading of eyes movement, processing of audible communication, etc.), and open communication mode, which is a communication that is initiated by the patient and being recorded by the communication module and can trigger operations, such as playing music, calling for a caregiver, communicating with a family member, etc.

The processing circuitry 252 is configured to receive input data ID being indicative of the sedation state of the patient and processing it to determine the sedation state of the subject. Based on said determination, the processing circuitry transmits execution data ED to the communication module 252 to trigger a selected communication protocol CP in the selected communication type. In response to receiving the execution data ED, the communication protocol outputs the required communication protocol CP to the patient.

FIG. 2B differs from FIG. 2A by showing that the system further comprising a sensing unit 256 that records sensed data of the patient (that can be a record of eye movements, EEG signals, EOG signals, a record of head gestures, microphone, etc.) and generates sensed input data SID indicative of the sedation state of the patient and transmits it to the processing circuitry 254 to process the data and determine the sedation state of the patient.

The invention claimed is:

1. A system for interacting with a patient, comprising:

a communication module configured to operate in at least three communication modes that comprise:

(1) unidirectional mode, in which the communication module outputs communication to the patient that does not require his/her response, (2) responsive mode, in which the communication module outputs communication to the patient that requires his/her response, the responsive mode comprises questions to or requests from the patient, and (3) open communication mode, in which the communication module allows the patient to proactively initiate communication with the system; and a processing circuitry that comprises an input module configured to receive input data indicative of the patient sedation state, the processing circuitry is configured to:

i. determine the sedation state of the patient based on the input data; and ii. trigger the communication module to operate in a selected communication mode in response to the determined sedation state;

wherein the determination of the sedation state of the patient based on the input data comprises classifying the sedation state of the patient into one of at least three sedation levels, each level triggers one or more level-specific communication modes;

wherein said classifying comprises scoring the sedation state of the patient, the score defines the sedation level, wherein three ranges of scores define the sedation levels, each range defines a different level; and wherein the processing circuitry is configured to:

trigger the unidirectional mode upon determining a non-responsive sedation state of the patient;

trigger the responsive mode and/or the unidirectional mode upon determining a low-level responsive sedation state of the patient;

trigger the open communication mode and/or the responsive mode and/or the unidirectional mode upon determining a high-level responsive sedation state of the patient;

wherein the scoring is a Richmond Agitation-Sedation Scale (RASS) score.

2. The system of claim 1, wherein the communication module is configured to perform and/or allow the patient audible communication, video-based communication, eye-based communication, touchscreen-based communication, tactile communication, EEG-based communication, EOG-based communication, automatic lip-reading communication, head gestures-based communication, or any combination thereof.

3. The system of claim 1, wherein the sedation state of the patient is the delirium state of the patient.

4. The system of claim 1, wherein said input data comprises recorded communication of the patient with the communication module.

5. The system of claim 1, wherein said input data comprises eye image data indicative of recorded images of an eye of the patient.

6. The system of claim 1, comprising a camera unit configured for recording images of an eye of the patient and generating eye image data based thereon, wherein said input data comprises said image data.

7. The system of claim 1, wherein said input data comprises EEG data indicative of recorded EEG signals of the patient.

8. The system of claim 1, comprising an EEG unit configured for recording EEG signals of the patient and generate EEG data based thereon, said input data comprises said EEG data.

9. A method for interacting with a patient, comprising:

receiving and processing input data indicative of the patient sedation state;

determining based on the input data the sedation state of the patient; and in response to the determined sedation state of the patient, outputting by a communication module a selected communication in a communication mode selected from at least one of three communication modes that comprises: (1) unidirectional mode, in which the communication module outputs communication to the patient that does not require his/her response, (2) responsive mode, in which the communication module outputs communication to the patient that requires his/her response, the responsive mode comprises questions to or requests from the patient, and (3) open communication mode, in which the communication module allows the patient to proactively initiate communication with the system;

wherein the determination of the sedation state of the patient based on the input data comprises classifying the sedation state of the patient into one of at least three sedation levels, each level triggers one or more level-specific communication modes;

wherein said classifying comprises scoring the sedation state of the patient, the score defines the sedation level, wherein three ranges of scores define the sedation levels, each range defines a different level;

wherein said outputting comprises:

selecting the unidirectional mode upon determining a non-responsive sedation state of the patient;

selecting the responsive mode and/or the unidirectional mode upon determining a low-level responsive sedation state of the patient;

selecting the open communication mode and/or the responsive mode and/or the unidirectional mode upon determining a high-level responsive sedation state of the patient;

wherein the scoring is a Richmond Agitation-Sedation Scale (RASS) score.

10. The method of claim 9, wherein said selected communication is any one of audible communication, video-based communication, eye-based communication, touch-screen-based communication, tactile communication, EEG-based communication, EOG-based communication, automatic lip-reading communication, head gestures-based communication, or any combination thereof.

11. The method of claim 9, wherein the sedation state of the patient is the delirium state of the patient.

12. The method of claim 9, wherein said input data comprises recorded communication of the patient with the communication module.

13. The method of claim 9, wherein said image data comprises eye image data indicative of recorded images of an eye of the patient.

14. The method of claim 9, wherein said input data comprises EEG data indicative of recorded EEG signals of the patient.

* * * * *